United States Patent
Malewicz

(10) Patent No.: US 8,777,893 B2
(45) Date of Patent: Jul. 15, 2014

(54) VARIABLE HEMOSTASIS VALVE AND METHOD OF USE

(75) Inventor: Andrzej Malewicz, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 566 days.

(21) Appl. No.: 13/084,124

(22) Filed: Apr. 11, 2011

(65) Prior Publication Data

US 2011/0251565 A1   Oct. 13, 2011

Related U.S. Application Data

(60) Provisional application No. 61/322,527, filed on Apr. 9, 2010.

(51) Int. Cl.
  *A61M 1/00* (2006.01)
  *A61M 5/178* (2006.01)
  *A61M 5/00* (2006.01)

(52) U.S. Cl.
  USPC .......................... 604/32; 604/167.01; 604/250

(58) Field of Classification Search
  USPC .................. 604/32, 34, 506, 164.01, 164.02, 604/167.01, 167.03, 167.05, 246, 248, 250, 604/256
  See application file for complete search history.

(56) References Cited

U.S. PATENT DOCUMENTS

| | | | | |
|---|---|---|---|---|
| 5,158,553 A | * | 10/1992 | Berry et al. | 604/248 |
| 5,935,122 A | * | 8/1999 | Fourkas et al. | 604/523 |
| 7,172,580 B2 | * | 2/2007 | Hruska et al. | 604/248 |
| 2005/0171479 A1 | * | 8/2005 | Hruska et al. | 604/167.06 |
| 2008/0157017 A1 | * | 7/2008 | Macatangay et al. | 251/314 |
| 2008/0208175 A1 | * | 8/2008 | Beckman et al. | 606/1 |

* cited by examiner

Primary Examiner — Andrew Gilbert

(57) ABSTRACT

A variable hemostasis valve is disclosed that may be used during medical procedures to prevent blood loss while permitting the percutaneous introduction, operation, and removal of medical instruments. A flexible tubular seal element is disclosed that is disposed within the variable hemostasis valve to provide a fluid-tight, adjustable seal. After insertion of a medical instrument into the valve through at least a portion of the flexible tubular seal element, a proximal portion of the valve housing may be rotated to cause the tension of the flexible tubular seal element to increase over the inserted medical instrument and engage the valve in a closed position. The proximal portion of the valve housing may then be rotated in an opposite direction to release the seal and return the tubular seal element to a relaxed lumen open position.

10 Claims, 8 Drawing Sheets

VARIABLE HEMOSTASIS VALVE AND METHOD OF USE

CROSS-REFERENCE TO RELATED APPLICATION

This application claims the benefit of U.S. Provisional Application No. 61/322,527, filed Apr. 9, 2010, which is incorporated by reference herein in its entirety.

FIELD OF THE INVENTION

The present invention is generally directed to a device used in conjunction with percutaneous medical procedures. More particularly, the present invention is directed to a variable hemostasis valve and a method for operating a variable hemostasis valve to enable the reduction of unintended bleeding and fluid leakage during a percutaneous medical procedure.

BACKGROUND OF THE INVENTION

Hemostasis valves are well known and used in a variety of percutaneous medical procedures that require the insertion of a catheter or other instruments and devices into a patient's body. For example, hemostasis valves enable the introduction and operation of catheters and other instruments into a patient's cardiovascular system during a minimally invasive interventional procedure. Typically, a guide catheter or introducer is connected to a distal end of the hemostasis valve, and an operating instrument is inserted into a proximal end and through the guide catheter or introducer to a desired location in the patient. Once the instrument is in place, the valve is closed around the instrument, thereby establishing a seal to prevent blood from escaping from the body of the patient.

Existing hemostasis valves, however, generally do not allow variable control over the strength of the seal within the hemostasis valve. Rather, most hemostasis valves use flaps or other zero-closure valves that simply move into different positions as the instrument is inserted through the valve. These flaps often fail to form a fluid-tight seal around the full structure of the inserted instrument, thereby allowing fluids to escape past the valve. Additionally, many hemostasis valves do not fully adapt to large or irregularly sized instruments. This results in unintended leakage and bleeding despite the use of the hemostasis valve during medical procedures.

BRIEF SUMMARY OF THE INVENTION

The present invention addresses these and other limitations of existing hemostasis valve assemblies by providing a variable hemostasis valve with a controllable seal that is easily opened or closed. The valve may be operated to be in a fully or substantially fully open position prior to percutaneous insertion of a medical instrument, thereby allowing full placement of the instrument into the patient's body with no interference from the hemostasis valve. After the instrument is inserted, the valve may be operated to tighten its seal around the medical instrument. Finally, the valve may be operated to release its seal and return to a fully or substantially fully opened position, enabling the extraction of any inserted medical instruments. Further, the variable hemostasis valve contains a series of locking guides to maintain various rotation positions, thereby allowing the valve seal to maintain an orifice size in a desired open or closed state with a set amount of seal pressure.

The interior of the presently described variable hemostasis valve assembly provides a form-fitting sealing tube or tubular seal element that defines a lumen passageway. The tubular seal element is made from a flexible tube of an elastomeric material that conforms and adapts to the shape of the various instruments that may be inserted therethrough. The tubular seal element is defined by a generally open cylindrical shape that allows insertion of instruments through a lumen or passageway thereof with little or no interference. The valve assembly may be rotated from an open position to a closed, sealed position. The valve assembly is rotated to cause rotation or "twisting" of the tubular seal element to sealingly engage the instrument. The flexible elastomeric tubular seal element is structured to return to a fully open position when counter-rotated, which provides discrete "closed" and "open" settings of the valve. A diameter of the passageway of the tubular seal element, which may be considered an orifice of the valve assembly, depends on how tightly the tubular seal element is twisted.

In an embodiment, the variable hemostasis valve is operably coupled to an introducer element, the introducer element being a cylindrical shaft having a removable conical tip coupled thereto. The conical tip or dilator is used to dilate the passage into which the introducer is introduced, while the introducer facilitates the insertion of some medical instrument directly into the patient's body. In use, the variable hemostasis valve is generally positioned outside the patient's body, allowing access to internal systems such as a patient's vascular system through the introducer while preventing blood from escaping. The conical tip functions as a dilator to allow introduction into the bodily space of the cylindrical shaft portion of the introducer. The variable hemostasis valve further provides a user, such as a surgeon, with a variable control seal to engage after insertion of the instrument and to release prior to extraction of the instrument.

Thus, the presently described hemostasis valve is structured to provide variable control of the tubular seal element suspended within the valve. In one embodiment, the valve provides a rotatable structure of the valve body that may be rotated by an operator to cause the tubular seal element to close around and seal against an instrument inserted into the introducer in a closed or sealed position, and likewise the rotatable structure of the valve body may be counter-rotated to cause the tubular seal element to return to an open position.

A variable hemostasis valve assembly disclosed according to an embodiment hereof is structured from a valve body having a tubular seal element positioned therein. The valve body includes a proximal housing portion rotatably secured to a distal housing portion. The tubular seal element is positioned such that a passageway thereof forms a midsection of a through lumen of the valve assembly. The tubular seal element has a proximal end operably coupled to the proximal housing portion and a distal end operably coupled to the distal housing portion. The proximal housing portion is further structured to be rotatably received by the distal housing portion, such that the tubular seal element may be rotated to selectively permit fluid flow through the lumen of the valve assembly in an open position or restrict fluid flow through the lumen of the valve assembly in a closed position. Further, the passageway extending through the tubular seal element is structured of a sufficient size and orientation to permit the introduction and extraction of a medical instrument in the open position, and the maintenance of a fluid tight seal around the inserted medical instrument in the closed position.

A method of use for the variable hemostasis valve according to one embodiment of the present invention may be performed to prevent blood loss while permitting the introduction of intravascular instruments into a patient's body. This method includes first inserting an instrument into the variable hemostasis valve, the lumen of the variable hemostasis valve being defined by a hollow tubular sealing element suspended between and inside two rotatably connected portions of the variable hemostasis valve assembly. Next, the proximal end of the variable hemostasis valve is rotated in a first direction, which causes the tubular element to twist and establish a seal around the instrument. After use of the instrument, the variable hemostasis valve is rotated opposite the first direction, to cause the tubular element to release the seal. Finally, after operation and release of the seal, the instrument may be extracted from the variable hemostasis valve.

DETAILED DESCRIPTION OF THE INVENTION

Specific embodiments of the present invention are now described with reference to the figures. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The presently disclosed variable hemostasis valve apparatus and method of use provide significant advantages over existing hemostasis valves. In addition to providing a fluid-tight seal, the seal is easily tightened and released by an operator through rotation of a proximal portion of the variable hemostasis valve housing. The presently disclosed variable hemostasis valve also provides a flexible, form-adapting seal which can be variably tightened and released upon command. Therefore, the valve may be used in conjunction with a number of insertion assemblies, instruments, and medical devices of varying shapes and sizes.

In one embodiment, the variable hemostasis valve is structured in a generally cylindrical shape for attachment to a tubular-shaped introducer. Those of ordinary skill in the art will appreciate however that the lumen defined within the cylindrical housing is structured to accept and seal medical instruments that are ultimately inserted into a passageway, organ or tissue of a patient. Further, the variable hemostasis valve provides a rotatable structure that can be activated after insertion of the instrument to operably tighten a cylindrical tubular seal within the variable hemostasis valve. FIGS. 1A-1D illustrate the structural components of this generally cylindrical variable hemostasis valve 100 according to selected embodiments of the present invention.

Figure 1A:
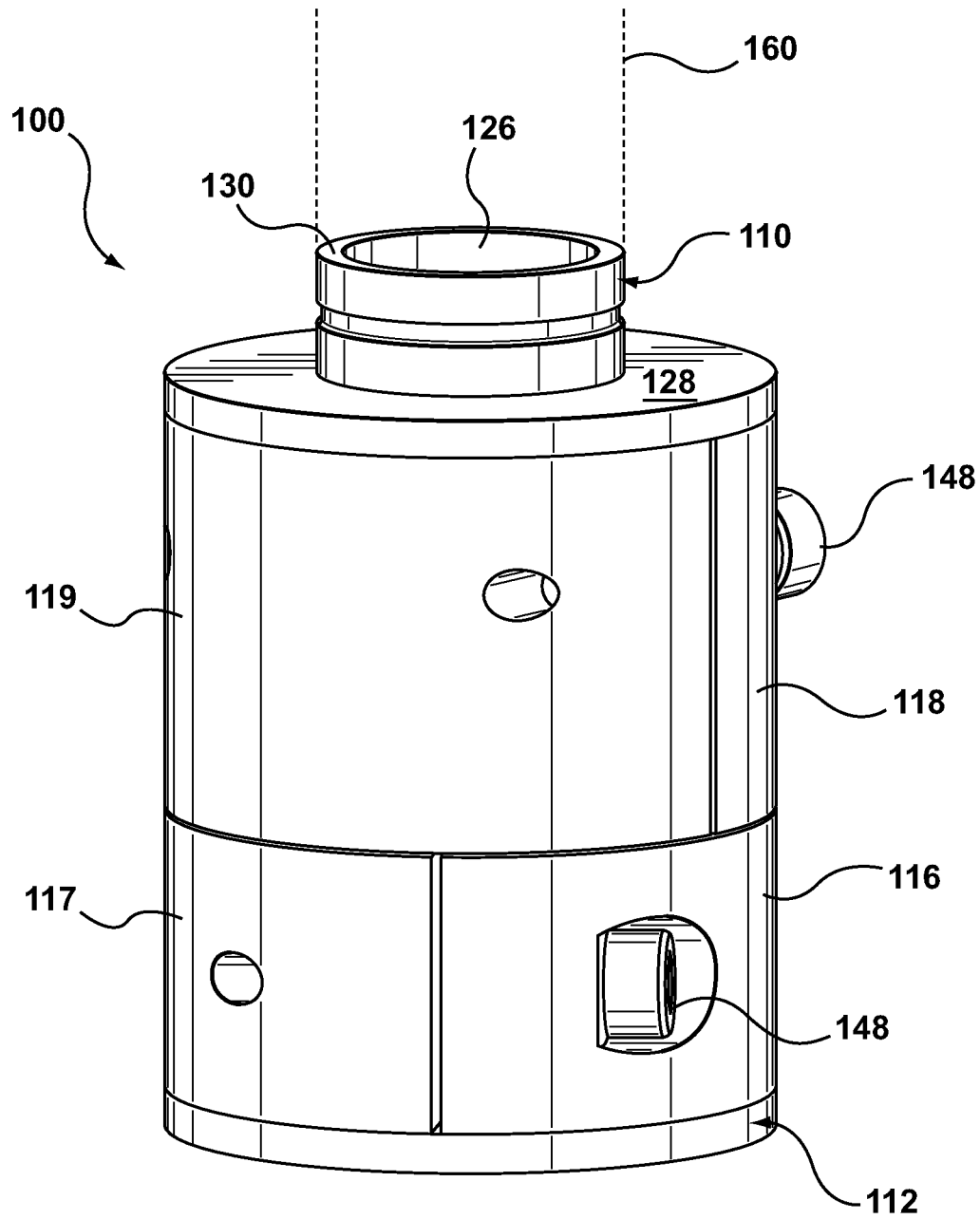
FIG. 1A is a perspective view of a variable hemostasis valve assembly according to an embodiment hereof.
Figure 1B:
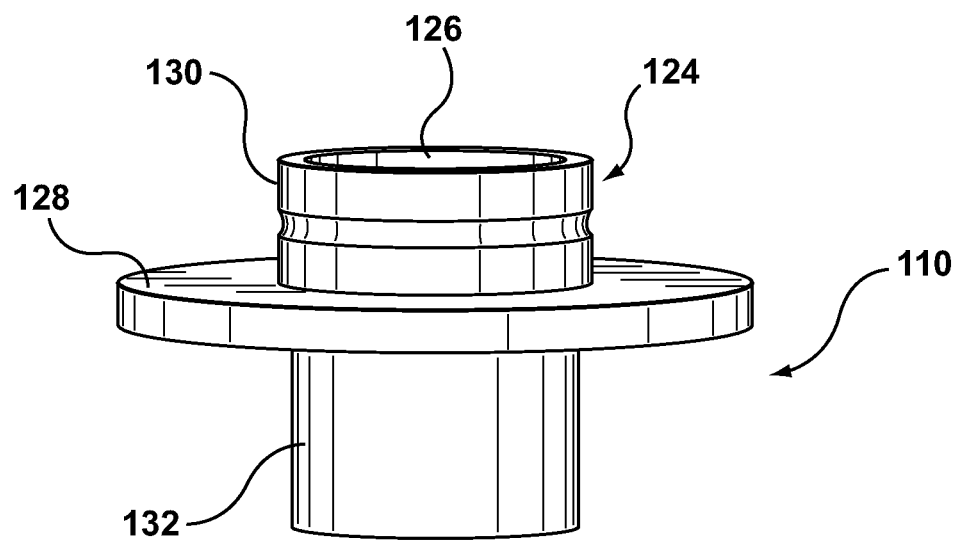
FIG. 1B is a perspective view of the distal portion of a variable hemostasis valve assembly according to an embodiment hereof.
Figure 1C:
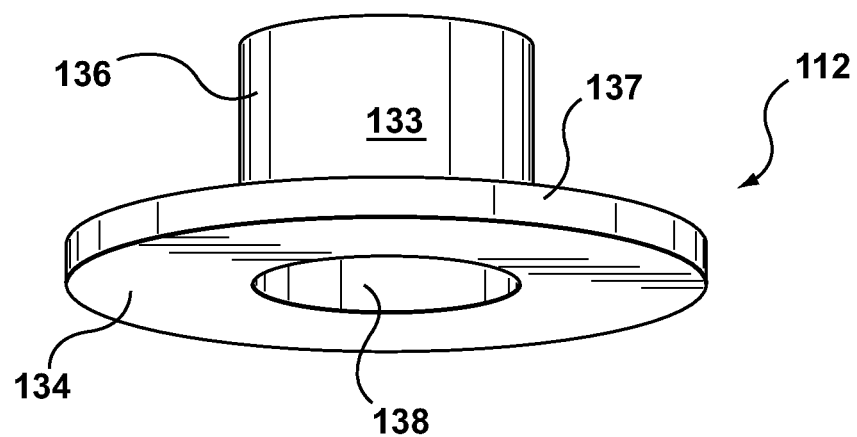
FIG. 1C is a perspective view of the proximal portion of a variable hemostasis valve assembly according to an embodiment hereof.
Figure 1D:
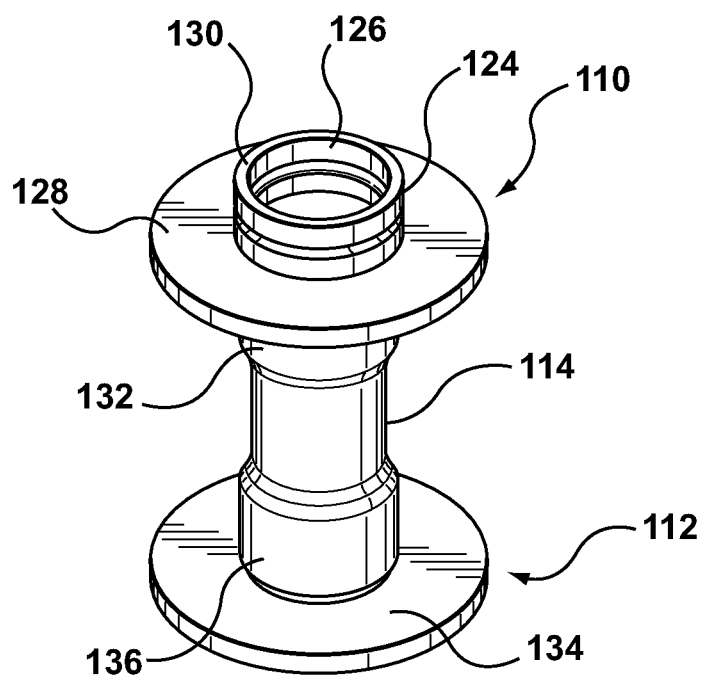
FIG. 1D is a perspective view of the tubular element positioned between the distal portion and the proximal portion of a variable hemostasis valve assembly according to an embodiment hereof.
Figure 6B:
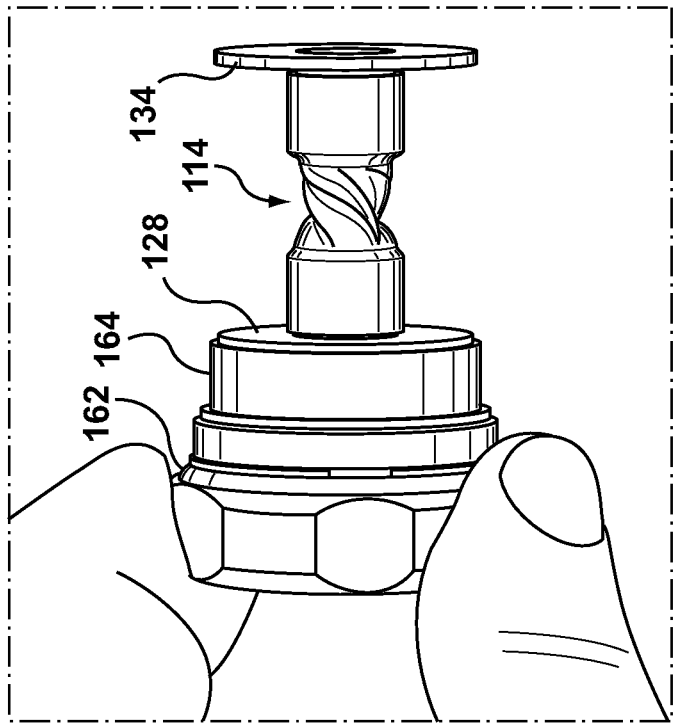
FIGS. 6A and 6B provide side views of a tubular seal element in an open, unsealed position and in a restricted, sealed position, respectively, according to an embodiment hereof.
Figure 6A:
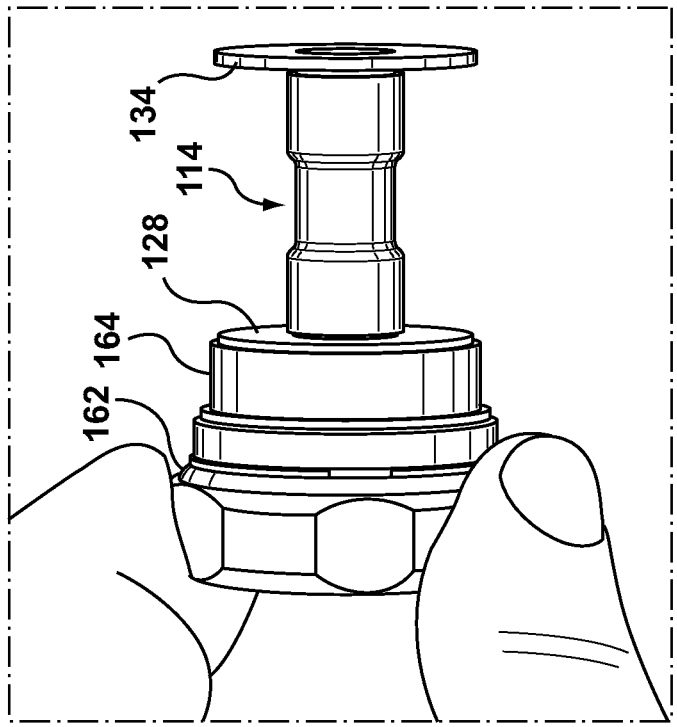

As shown in FIG. 1A, the variable hemostasis valve 100 includes distal and proximal flange portions 110, 112 on the distal and proximal ends of the valve 100 respectively (the distal and proximal flange portions are further depicted in FIGS. 1B and 1C respectively). The variable hemostasis valve includes a flexible tubular seal element 114 (as best seen in FIG. 1D and FIGS. 6A-6B), first and second male portions 116, 117 coupled with fasteners 148, and first and second female portions 118, 119 coupled with second fasteners 149. Fasteners 148, 149 may include screws, pegs, and the like. Alternatively first and second male and female portions may be fixedly coupled with glue, epoxy, adhesives, and the like. Distal flange portion 110 is structured to operably engage with an introducer or other assembly 160 that may be inserted into the patient's vascular system or other body location. In practice, distal flange portion 110 is operably coupled to introducer 160 through methods known to those of ordinary skill in the art (such as with an adhesive, fasteners, and the like).

Referring to FIG. 1B, distal flange portion 110 includes tubular element 124 defining a lumen 126 therewithin. Tubular element 124 is operably engaged to disc 128. Tubular element 124 includes distal end 130 and proximal end 132. As best seen in FIG. 1A, the lumen 126 of the tubular element 124 extends into the interior of the hemostasis valve 100 when operably coupled thereto, and may be surrounded by first and second female portions 118, 119.

As seen in FIG. 1C, proximal flange portion 112 includes a second tubular element 133 including disc 134 coupled to proximal end 137, opposite the distal end 136. Second tubular element 133 defines a lumen 138 there within.

As seen in FIG. 1D, a first end of tubular seal element 114 is slightly stretched to be force fit and engaged over distal end 136 of proximal flange portion 112 and a second end is slightly stretched to be force fit and engaged over proximal end 132 of distal flange portion 110. As such at least a mid-section of the tubular seal element 114 is therefore suspended or bridged between flange portions 112, 110 for defining a passageway between lumen 126 of distal flange portion 110 and lumen 138 of proximal flange portion 112. In one embodiment, tubular seal element 114 is a hollow, cylindrical tube that is made from stretchable, form-fitting material such as latex. Those of ordinary skill in the art will appreciate that other types of flexible and/or elastomeric materials may be suitable to serve as a tubular seal element of the presently disclosed valve such as nitriles, propylenes, silicones, and the like.

After tubular seal element 114 is formed and suspended between the flange portions 112, 110, the flange portions are surrounded by a proximal housing component formed from male portions 116, 117 and a distal housing component formed from female portions 118, 119 to collectively form a valve housing around the flange portions and tubular seal element 114 that is disposed within the variable hemostasis valve. More particularly, male portions 116, 117 of the housing are secured to each other to clamp around distal end 136 of proximal flange portion 112 and the portion of tubular seal element 114 secured thereover and female portions 118, 119 of the housing are secured to each other to clamp around proximal end 132 of distal flange portion 110 and the portion of tubular seal element 114 secured thereover. Those of ordinary skill in the art would recognize that the male portions 116, 117 and female portions 118, 119 may be of an opposite orientation (specifically, proximal portions 116, 117 may be female and distal portions 118, 119 may be male), provided of course that each set of portions is structured to be rotatably coupled with each other. In either case, the variable hemostasis valve is configured so that the portion proximal to the operator is structured to rotate and effectuate the variable valve seal.

Figure 2:
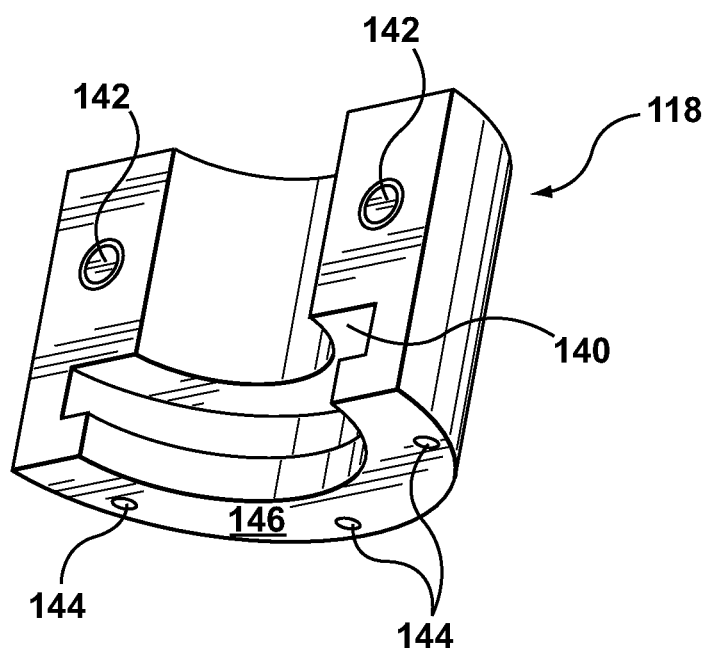
FIG. 2 is a cross-sectional view of a female portion used in the housing of a variable hemostasis valve assembly according to an embodiment hereof.

Referring to FIG. 2, female portion 118 includes an interlocking channel 140, optional openings 142 for receiving fasteners 148, and a plurality of dimples 144 on a proximal contact surface 146 thereof. Male portion 116, illustrated in FIG. 3, includes optional openings for receiving fasteners 148 and an interlocking flange 150 extending longitudinally from a top surface 151 thereof. Interlocking flange 150 mates and interlocks with interlocking channel 140 of female portion 118, with the interlocking channel permitting rotation between the male and female portions.

Figure 3:
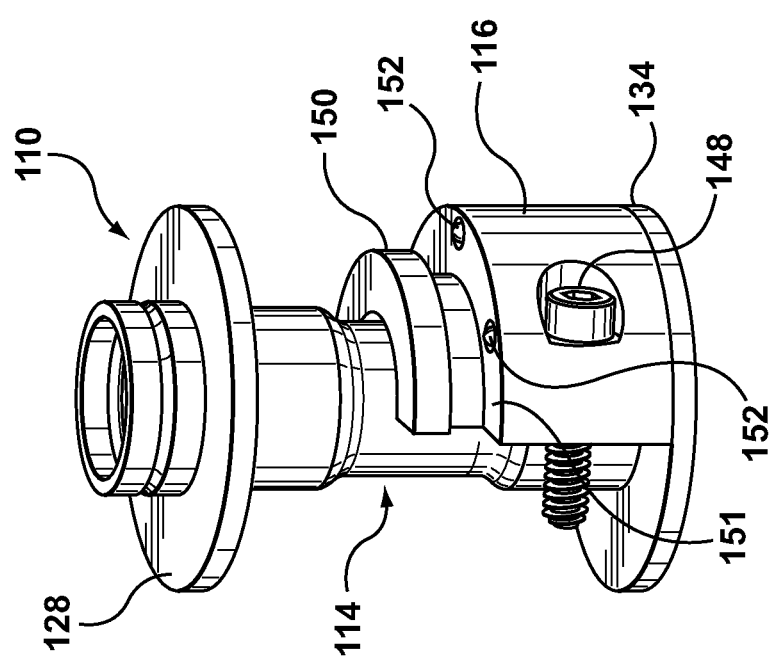
FIG. 3 is a cut away view of a male portion used in the housing of a variable hemostasis valve assembly according to an embodiment hereof.

A distal contact surface 151 of male portion 116, 117 includes a plurality of spring-loaded ball plungers 152. Spring-loaded ball plungers 152 are biased outwardly in the extended position to matingly engage with dimples 144 on female portion 118, 119 and thereby form a series of locking guides of the housing that secure a rotational position of the proximal housing component relative to the distal housing component. Thus, when an operator rotates male portion 116, 117 relative to female portion 118, 119, spring-loaded ball plungers 152 contact and engage dimples 144 creating a "stop". The spring-loaded nature of the plungers 152 allow tubular seal element 114 attached to the male portion of the variable hemostasis valve to be rotated and twisted with minimal force, while still allowing for a rotational position to be maintained and therefore tubular seal element 114 to remain engaged or disengaged in a specific position. Although FIG. 3 depicts three sets of dimples 144 and ball plungers 152 on each half of the male and female portions, those of ordinary skill in the art would recognize that the number of dimples and plungers depends on the size of valve 100, the size of the dimples and plungers, and the amount of force exerted on the dimples and plungers by valve 100 and flexible tubular seal element 114.

Figure 4:
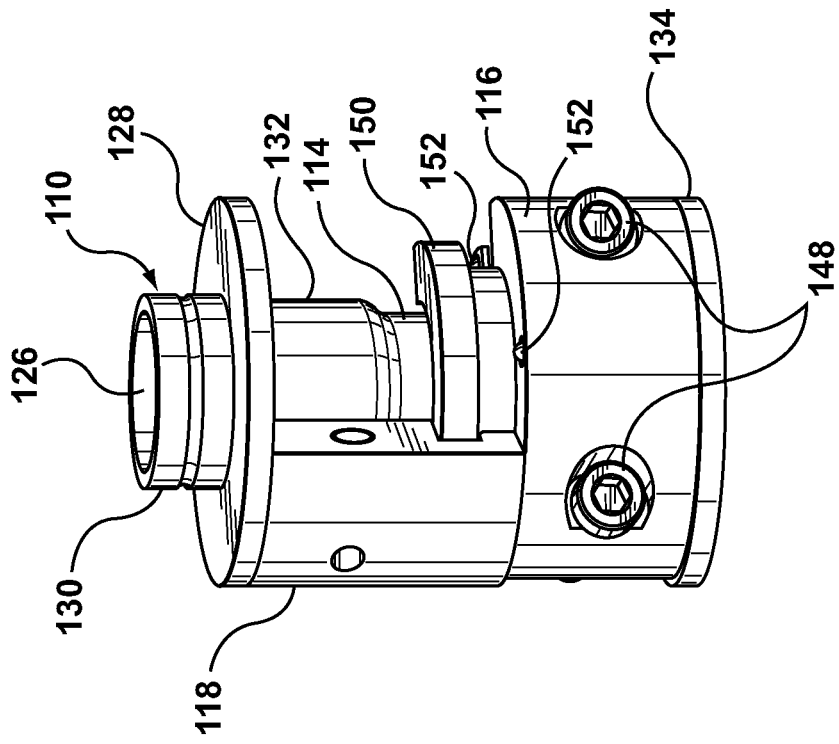
FIG. 4 provides a cut-away view of coupled female and male housing portions of the variable hemostasis valve assembly according to an embodiment hereof.

FIG. 4 further depicts the structure enabling the rotation of the proximal, male portions 116, 117 within the hemostasis valve, the structure causing the tubular seal element 114 to be twisted or untwisted and therefore the seal to be variably engaged or released within hemostasis valve 100.

Disc 128 of distal flange portion 110 fixedly engages with a distal contact surface of female portions 118, 119 (female portion 119 being removed in FIG. 4) when female portions 118, 119 are secured to one and other by fasteners 148 to fixedly clamp around proximal end 132 of distal flange portion 110 and the portion of tubular seal element 114 secured thereover. Disc 134 of proximal flange portion 112 fixedly engages with a proximal contact surface of male portions 116, 117 (male portion 117 being removed in FIG. 3) when male portions 116, 117 are secured to one and other by fasteners 148 to fixedly clamp around distal end 136 of proximal flange portion 112 and the portion of tubular seal element 114 secured thereover. The male portion 116 is depicted as using screw-like fasteners 148 to attach to male portion 117, although those of ordinary skill in the art would recognize that other types of fasteners and attachment mechanisms or compositions could be used in place thereof.

As an illustration of a method of use for the previously described embodiment, a surgeon inserts the variable hemostasis valve 100 that is operably coupled an introducer 160 (shown in FIG. 7) into the vasculature of the patient. An instrument is inserted into and through the lumen of valve 100 that is created by lumens 138, 126 and the lumen of tubular seal element 114, as the tubular seal element 114 within valve 100 remains in a fully open or substantially open position. Male portions 116, 117 may be rotated clockwise or counter clockwise relative to female portion 118, 119. As the male portions 116, 117 are rotated, spring-loaded ball plungers 152 positioned around the outside circumference of the male portions 116, 117 commence contact with and engage the various dimples 144 positioned around the outside circumference of the female portions 118, 119. The tubular seal element 114 between lumens 126, 138 in turn commences to twist and close around an instrument inserted within the lumen thereof to form a fluid-tight seal. Further rotation of male portions 116, 117 relative to female portions 118, 119 rotates the ball plungers 152 to a next adjacent dimple 144 while the tubular seal element 114 flexes and tightens further around the surgical instrument therein.

The lumen defined within the hemostasis valve, when coupled to an introducer, provides an internal longitudinal passage dimensioned to permit passage of a variety of sizes and shapes of surgical instrumentation. The diameter of the lumen provided within the variable hemostasis valve will vary depending on the size of the valve body and the tubular seal, and the particular surgical application as required by the introducer assembly. In one embodiment, the lumen and tubular seal within the variable hemostasis valve is configured to allow hemostasis with devices ranging from under 1 mm to approximately 12 mm in diameter.

The housing of the variable hemostasis valve (specifically the female and male portions 116, 117, 118, 119 and the distal and proximal flange portions 110, 112) may be formed with any number of rigid materials, preferably a polymeric material such as medical grade polycarbonate. The male and female portions may be clear or opaque, although being clear provides the advantage of allowing the user with a view of the overall state and position of the internal seal and any liquids that may reach the point of the seal.

Figure 5B:
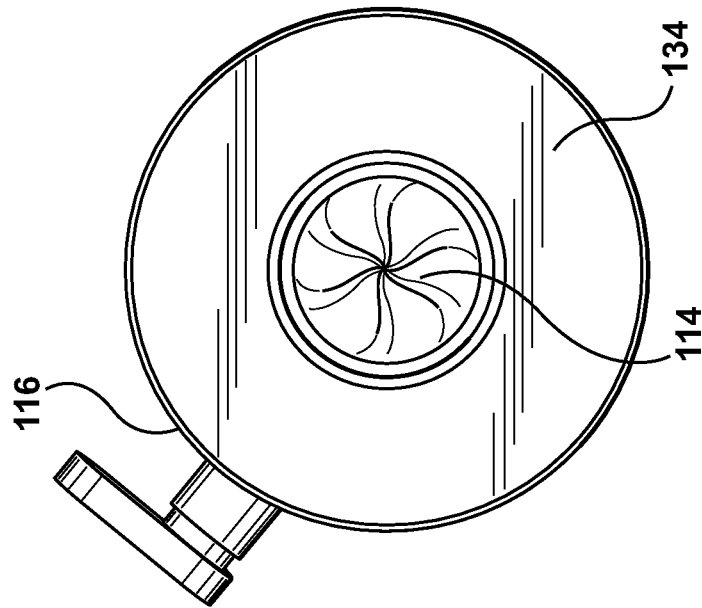
FIG. 5A provides a proximal view of a variable hemostasis valve having its tubular seal element providing an open passageway and FIG. 5B provides a proximal view of the variable hemostasis valve having its tubular seal element providing a closed passageway according to an embodiment hereof.
Figure 5A:
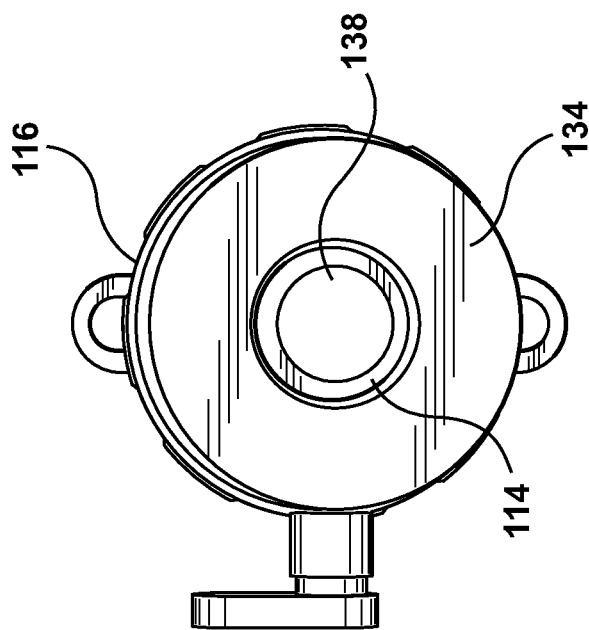

FIG. 5A provides a view of the proximal end 134 of the variable hemostasis valve, having an internal sealing member held in a fully opened position to receive a medical instrument. As shown, the passageway 138 within the tubular seal element 114 is unrestricted to allow insertion of an operating instrument through the valve. In this position, tubular seal element 114 remains in its original relaxed or untwisted position. FIG. 5A also shows the location of half of male portion 116, which in combination with the other half of male portion 117 (not shown in FIG. 5A) can be rotated by an operator to control the valve seal of the tubular seal element 114.

FIG. 5B illustrates the state of the internal tubular seal element 114 after the male portions 116, 117 of the variable hemostasis valve 100 are rotated, causing the tubular seal element 114 to engage and result in a fully closed seal position. Any instrument or device inserted through the lumen of tubular seal element 114 prior to engaging the seal will result in the seal wrapping around the instrument or device. Further, the flexible nature of the seal (such as through the use of a latex tube) allows the inserted instrument to possess a limited range of movement, allowing some movement about a longitudinal axis intersecting the center of the valve lumen.

FIGS. 6A and 6B provide an enhanced illustration of the tubular seal element 114 in an open, untwisted position and in a closed, twisted position respectively according to an embodiment hereof. These drawings illustrate the structure of the variable hemostasis valve with the male and female housing portions not attached. The tubular seal element 114 is coupled only to the distal flange portion 110 and the proximal flange portion 112 (as evidenced by the depiction of disc 128 and 134). As shown, the disc 128 of the distal flange portion 110 is coupled to a screw-locking cap 162 of an introducer assembly 164; the proximal flange portion 112 is depicted as not being attached to any other structure.

As shown in FIG. 6A, the tubular seal element 114 is in its relaxed state having a full inner diameter to allow insertion of instruments and objects within its internal passageway. FIG. 6B indicates the state of the tubular seal element 114 upon rotation of the proximal flange portion 112. As the proximal flange portion 112 rotates either clockwise or counter-clockwise, the flexible tubular seal element 114 twists to constrict its lumen. The flexible nature of the seal material, such as elastomeric latex, allows a fluid- and/or gas-tight seal to be formed as tension is increased and the seal material is stretched around any instrument inserted therethrough. The flexibility of the seal material however, allows a range of movement and allows operability of the instrument. Ultimately, when the proximal flange portion 112 is rotated in the opposite direction, the tension on the tubular seal element 114 will release, and the flexible tubular seal element 114 will return to its previous relaxed state as shown in FIG. 6A.

Figure 7:
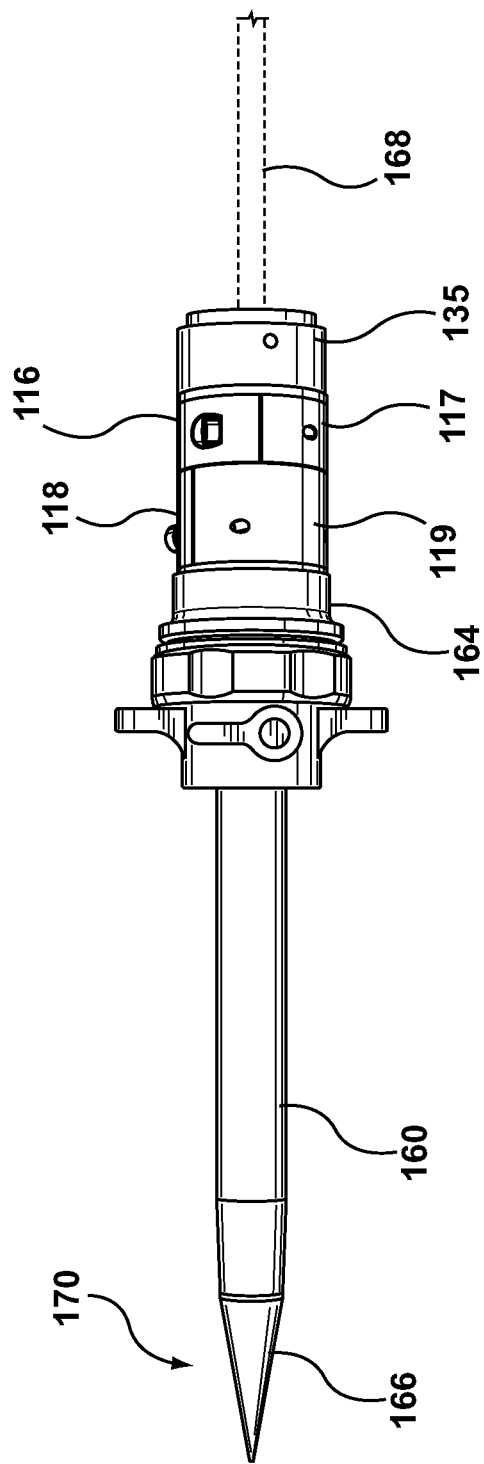
FIG. 7 is a perspective view of an introducer assembly operably coupled to a variable hemostasis valve according to an embodiment of the invention.

FIG. 7 provides an illustration of a device assembly containing the variable hemostasis valve 100 operably coupled to a removable portion 164 of an introducer 160. A dilator assembly 170 with a proximal end 135 is shown extending through introducer 160 with a pointed tip 166 thereof allowing surgical insertion into a patient's body. Upon removal of dilator assembly 170 a medical instrument 168 for percutaneous introduction is illustrated as being insertable into the lumen of the hemostasis valve, and ultimately into and through the introducer 160. As shown, male portions 116, 117 that are rotatable by the operator are proximal to female portion 118, 119 (with 119 not shown in FIG. 7).

Those of ordinary skill in the art would recognize that other introducer assemblies and devices may be coupled to the presently disclosed embodiments of the variable hemostasis valve and used in conjunction with the presently disclosed methods of use. Moreover, although the present invention has been described with reference to preferred embodiments, those of ordinary skill in the art will also recognize that changes may be made in form and detail without departing from the spirit and scope of the invention.

What is claimed is:

1. A variable hemostasis valve, comprising:
    a valve body having a proximal housing component that is rotatable relative to a distal housing component, wherein the valve body includes a proximal flange portion forming a proximal segment of a valve body lumen and a distal flange portion forming a distal segment of the valve body lumen; and
    a tubular seal element defining a fluid passageway between a proximal end and a distal end thereof, the tubular seal element being disposed within the valve body between the proximal flange portion and the distal flange portion such that the fluid passageway forms a midsection of the valve body lumen that is in fluid communication with the respective proximal and distal segments of the valve body lumen,
    wherein the proximal housing component includes first and second portions that are securable together to surround and clamp the proximal flange portion and a first segment of the tubular seal element therebetween and wherein the distal housing component includes first and second portions that are securable together to surround and clamp the distal flange portion and a second segment of the tubular seal element therebetween such that the proximal end of the tubular seal element is operably coupled to the proximal housing component and the distal end of the tubular seal element is operably coupled to the distal housing component; and
    wherein upon the proximal housing component being rotated relative to the distal housing component, the tubular seal element may be selectively twisted between an open position that permits fluid flow through the fluid passageway and a closed position that restricts fluid flow through the fluid passageway.

2. The variable hemostasis valve of claim 1, wherein the tubular seal element is twistable to establish a seal around a medical instrument extending through the fluid passageway thereof.

3. The variable hemostasis valve of claim 1, wherein the tubular seal element is twistable to establish a seal around medical devices having various outer diameters.

4. The variable hemostasis valve of claim 1, wherein the tubular seal element is a tube of an elastomeric material.

5. A variable hemostasis valve, comprising:
    a valve body having a proximal housing component with a flange and a distal housing component with a channel within which the flange is received to permit rotation of the proximal housing component relative to the distal housing component;
    a tubular seal element defining a fluid passageway between a proximal end and a distal end thereof, the tubular seal element being positioned within the valve body such that the fluid passageway forms a midsection of a lumen through the valve body, wherein the proximal end of the tubular seal element is operably coupled to the proximal housing component and the distal end of the tubular seal element is operably coupled to the distal housing component such that when the proximal housing component is rotated relative to the distal housing component, the tubular seal element may be selectively twisted between an open position that permits fluid flow through the fluid passageway and a closed position that restricts fluid flow through the fluid passageway; and
    a series of locking guides disposed between the proximal housing component and the distal housing component to secure various rotational positions therebetween, wherein the series of locking guides includes dimples within a contact surface of one of the proximal and distal housing components that are engaged by spring-loaded ball plungers that extend from a corresponding contact surface of the other of the proximal and distal housing components.

6. The variable hemostasis valve of claim 5, wherein the tubular seal element is twistable to establish a seal around a medical instrument extending through the fluid passageway thereof.

7. The variable hemostasis valve of claim 5, wherein the tubular seal element is twistable to establish a seal around medical devices having various outer diameters.

8. The variable hemostasis valve of claim 5, wherein the valve body includes a proximal flange portion forming a proximal segment of the valve body lumen and a distal flange portion forming a distal segment of the valve body lumen.

9. The variable hemostasis valve of claim 8, wherein the tubular seal element is disposed between the proximal flange portion and the distal flange portion such that the fluid passageway thereof is in fluid communication with the respective proximal and distal segments of the valve body lumen.

10. The variable hemostasis valve of claim 5, wherein the tubular seal element is a tube of an elastomeric material.

* * * * *